United States Patent [19]

Engel et al.

[11] 4,322,441

[45] Mar. 30, 1982

[54] USE OF FLUORINATED BETA-DIKETONES AS BACTERIOCIDES AND FUNGICIDES

[75] Inventors: Michael R. Engel, White Bear Lake; Jill P. Stiller, Brooklyn Park, both of Minn.

[73] Assignee: Minnesota Mining and Manufacturing Company, St. Paul, Minn.

[21] Appl. No.: 259,702

[22] Filed: May 1, 1981

Related U.S. Application Data

[63] Continuation-in-part of Ser. No. 84,990, Oct. 15, 1979, abandoned.

[51] Int. Cl.³ .............................................. A01N 35/00
[52] U.S. Cl. .................................................... 424/331
[58] Field of Search ......................................... 424/331

[56] References Cited

U.S. PATENT DOCUMENTS

| | | | |
|---|---|---|---|
| 2,532,558 | 12/1950 | Kirby | 167/22 |
| 2,856,418 | 10/1958 | Calvin | 260/429.1 |
| 3,395,235 | 7/1968 | Litt | 424/331 |
| 3,636,214 | 1/1972 | Clark | 424/245 |
| 4,015,980 | 4/1977 | MacKay et al. | 75/120 |
| 4,031,246 | 6/1977 | Collins et al. | 424/331 |

FOREIGN PATENT DOCUMENTS 44-2823  2/1969  Japan .

Primary Examiner—Allen J. Robinson
Attorney, Agent, or Firm—Cruzan Alexander; Donald M. Sell; Lorraine R. Sherman

[57] ABSTRACT

This invention relates to a process for inhibiting the growth of bacteria and fungi on the animal body and on inanimate surfaces using certain fluorinated beta-diketones.

14 Claims, No Drawings

USE OF FLUORINATED BETA-DIKETONES AS BACTERIOCIDES AND FUNGICIDES

This is a continuation-in-part of U.S. patent application Ser. No. 84,990, filed Oct. 15, 1979, now abandoned.

TECHNICAL FIELD

This invention relates to a process for inhibiting the growth of bacteria and fungi on the animal body and on inanimate surfaces using fluorinated beta-diketones.

BACKGROUND ART

There is a continual need for bacteriocidal and fungicidal materials and, in particular, it is desirable to have these compositions available in vehicles suitable for medicinal use where control of bacteria is necessary.

For many years phenolics, guanidine derivatives, and iodine derivatives have been used as bacteriocides. All of these compositions exhibit undesirable properties, such as the causing of skin irritation, toxicity, corrosiveness or malodorousness when applied to the subject. Hexachlorophene, presently in limited use as a bacteriocide, has been identified as a possible carcinogen. There is a present need for bacteriocidal compositions which are safe, effective and pleasant to use.

Fungi have been found to infect skin, nails, mucous membrane, lungs and other organs of animals. Antifungal compositions in wide use include sulfur-containing compounds and antibiotic agents. The use of fluorinated beta-diketones, however, as fungicidal compositions has not previously been described in the art.

Beta-diketones are known particularly for their ability to chelate with various metals. For example, U.S. Pat. No. 4,015,980 teaches that zinc is extracted from aqueous ammoniacal solutions using certain $\beta$-diketones, and U.S. Pat. No. 2,856,418 discloses a process for separating plutonium from an aqueous solution of its tetravalent salt using certain fluorinated $\beta$-diketones.

U.S. Pat. No. 3,636,214 teaches that certain beta-diketones, some within the class of compounds of the instant invention, are soil fungicides and pesticides for plants. U.S. Pat. No. 3,395,235 discloses keto alcohols having two perfluoroalkyl groups thereon. These compounds are useful as nemotocides, i.e., for the killing of a specific class of elongated cylindrical worms. U.S. Pat. No. 2,532,558 discloses 1,2-dicarbonylethylene compounds having the formula

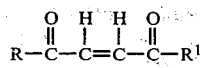

for the control of bacteria, fungi, and insects. Japanese Pat. No. 44-2823 teaches that acetophenone derivatives, which are not beta-diketones, are useful agricultural germicides. U.S. Pat. No. 4,031,246 discloses aryloxyalkyl diketones and keto esters as pesticidal and antiviral agents. However, there is no teaching in this patent as to bacteriocidal or fungicidal properties of such compounds.

DISCLOSURE OF THE INVENTION

In accordance with the present invention it has been found that certain beta-diketone compounds have useful bacterial growth inhibiting properties on the animal body (other than the oral cavity) and on inanimate surfaces. In addition, certain beta-diketone compounds have useful fungi growth inhibiting properties on the animal body and on inanimate surfaces. In particular it is found that certain beta-diketones inhibit the growth of a number of types of bacteria and fungi. The beta-diketones may be represented by the general formula

wherein Y is an alkyl group, an alkenyl group, or a halogen substituted alkyl or alkenyl group (limited as specified below under "Detailed Description"), phenyl or naphthyl or their halogen substituted derivatives, and $R_f$ is a perfluoroalkyl group containing one to three carbon atoms.

The fluorinated beta-diketones are made by a simple synthesis method starting from the corresponding methyl ketone compound, $Y-CO-CH_3$, and condensing this compound with a fluorocarbon ester such as ethyltrifluoroacetate in the presence of a base. The reactants are dissolved in a polar solvent, such as ethanol, and refluxed for from several minutes to several hours. The resulting compounds, when solid, may be recrystallized or, when liquid may be purified by distillation at reduced pressure.

Compounds described in this application are useful as dental antiplaque agents for control of *Streptococcus mutans* bacteria in the oral cavity and are described in assignee's copending application Ser. No. 257,700, filed on the same date as this application. The use of such compounds as dental anti-plaque agents, however, does not suggest the efficacy of the use of a growth inhibiting amount of such compounds for control of other types of bacteria on the animal body outside the oral cavity or on inanimate surfaces. Furthermore, the use of such compounds as dental anti-plaque agents does not suggest the efficacy of the use of a growth inhibiting amount of such compounds for fungicidal purposes.

DETAILED DESCRIPTION

The beta-diketone compounds which are useful in the present invention as bacteriocides on the animal body (other than the oral cavity) and on inanimate surfaces may be represented by the formula

   I wherein Y is an alkyl group having 5 to 20 carbon atoms, an alkenyl group having 5 to 20 carbon atoms, a halogen-substituted alkyl group having 5 to 20 carbon atoms, a halogen-substituted alkenyl group having 5 to 20 carbon atoms, a phenyl or naphthyl group or their halogen-substituted derivatives, and $R_f$ is a perfluoroalkyl group containing one to three carbon atoms. Preferred compounds for use in controlling the growth of bacteria are those compounds wherein Y is an alkyl group or an alkenyl group having 5 to 18 carbon atoms. Most preferred are beta-diketone compounds wherein Y is an alkyl group having 11 to 13 carbon atoms. Perfluoro beta-diketone compounds of small chain length (i.e., wherein Y of formula I is $C_4$ or less) are not effective against bacteria.

Beta-diketone compounds which are useful in the present invention as fungicides may be represented by formula I wherein Y is an alkyl group having 3 to 15 carbon atoms, an alkenyl group having 3 to 15 carbon atoms, or a halogen-substituted alkyl group having 3 to 15 carbon atoms, or a halogen-substituted alkenyl group having 3 to 15 carbon atoms, and $R_f$ is perfluoroalkyl group containing one to three carbon atoms. Preferred compounds for use in controlling the growth of fungi are those compounds wherein Y is $C_3$, $C_4$, $C_{11}$, and $C_{13}$.

Exempliary of beta-diketone compounds useful as both a bacteriocide and a fungicide are:
1,1,1,2,2-pentafluorodecanedione-3,5
1,1,1,2,2,3,3-heptafluoroundecanedione-4,6
1,1,1-trifluorononanedione-2,4
1,1,1-trifluoro-5-chlorononanedione-2,4
1,1,1-trifluorononene-5-dione-2,4
1,1,1-trifluoro-5-chlorononene-5-dione-2,4
1,1,1-trifluorodecanedione-2,4
1,1,1-trifluoropentadecanedione-2,4
1,1,1-trifluoroheptadecanedione-2,4

Additional exempliary beta-diketone compounds useful as a bacteriocide are:
1,1,1-trifluorooctadecanedione-2,4
1,1,1-trifluoro-5-chlorooctadecanedione-2,4
1,1,1-trifluorooctadecene-5-dione-2,4
1,1,1-trifluoroheneicosanedione-2,4
1,1,1-trifluorotetracosanedione-2,4
1,1,1-trifluoro-4-phenylbutanedione-2,4
1,1,1-trifluoro-4-(4-chlorophenyl)butanedione-2,4
1,1,1-trifluoro-4-(1-naphthyl)butanedione-2,4

Additional exempliary beta-diketone compounds useful as a fungicide are:
1,1,1-trifluoroheptanedione-2,4
1,1,1-trifluoro-5-chloroheptadione-2,4
1,1,1-trifluoroheptene-5-dione-2,4
1,1,1,2,2-pentafluorooctanedione-3,5
1,1,1,2,2-pentafluoro-6-chloroctene-6-dione-3,5
1,1,1-trifluorooctanedione-2,4
1,1,1-trifluorooctene-5-dione-2,4
1,1,1,2,2,3,3-heptafluorooctanedione-4,6

In the present invention, bacteriostatic and fungicidal activity of fluorochemical beta-diketones is assayed by a tube dilution technique in which 0.1 ml of a 24 hour culture of the particular bacterium in Trypticase Soy Broth (TSB) is added to a solution or dispersion containing dilutions ranging from 1000 to 0.01 ppm of solubilized candidate compound. Samples are taken periodically, plated out and examined to determined inhibition of growth as a function of time and concentration. Thus

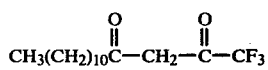

is tested against various organisms and is found to be effective in inhibiting growth of *Staphylococcus aureus* at a compound concentration of 3-5 ppm, and is effective at 10–33 ppm in inhibiting the growth of *Streptococcus faecalis*. Slight activity is also noted against the gram negative bacteria *Pseudomonas aeruginosa* and *Escherichia coli*.

The anti-bacterial and anti-fungi compositions are formulated by preparing a dilute solution or suspension in a vehicle or diluent such as an organic or aqueous-organic medium, for example, ethyl alcohol, acetone, dimethylsulfoxide, and the like, and are applied to the locus to be disinfected by conventional means such as spraying, swabbing or immersing. Alternatively, the compounds can be formulated for topical application in medicinal or veterinary use as ointments or creams by incorporating them in conventional ointment or cream bases, such as alkylpolyether alcohols, cetyl alcohol, stearyl alcohol and the like; as jellies by incorporating them in conventional jelly bases such as glycerin and tragacanth; or as aerosol sprays, foams or soaps. These compositions can be formulated for disinfection of inanimate surfaces by incorporation in vehicles that are aqueous or aqueous-organic solutions.

This invention is further illustrated by the following examples.

EXAMPLE 1

Compounds for use in the invention are prepared by condensation of lower alkyl trifluoroacetate, e.g. ethyl trifluoroacetate, with the appropriate alkanone using sodium alkoxide and subsequent acidification. This is illustrated by the following procedure.

A mixture of 11 g ethyltrifluoroacetate and 15 g methylundecylketone is gradually added over 15 minutes to a stirred solution of 2.0 g sodium metal in 75 ml ethanol in a 250 ml round bottomed flask. The mixture is refluxed for four hours and then allowed to stand overnight. The mixture solidifies and is decomposed by addition of 300 ml of 6 N hydrochloric acid. The oily organic phase is extracted with 150 ml ether, dried over anhydrous sodium sulfate, decanted, and the ether removed by evaporation. The resulting product, 1,1,1-trifluoropentadecandione-2,4, is a light yellow liquid distilling at 91° to 94° C. at 0.03 mm Hg. Yield is 12.5 gm.

A similar procedure using 2-octanone yields 1,1,1-trifluorodecandione-2,4 distilling at 40° C. to 42° C. at 0.1 mm Hg. A lower homolog, 1,1,1-trifluoroheptandione-2,4 (b.p. 80° at about 50 mm pressure) is prepared similarly and used for comparison purposes. Further similar procedures are employed to prepare 1,1,1-trifluoroheptadecandione-2,4 (b.p. 110° C., 0.08 mm.) and 1,1,1-trifluoroheneicosandione-2,4.

EXAMPLE 2

A number of the above compounds are tested for their ability to inhibit the growth of *Staphylococcus aureus* (a bacterium) and *Candida albicans* (a fungus) by placing solutions or dispersions of the compounds at various concentrations (expressed in parts per million) in small wells with a culture of the organism and determining the extent of growth of the organisms by the turbidity of the well. Data are recorded as "−" for no growth, "+" for normal growth with substantially no inhibition and "±" for slight inhibition of growth. Duplicate runs are made using the compounds identified by the respective Roman numerals in Table 1. In almost all cases identical results were obtained for duplicating tests. The results are tabulated in Table 2 for *S. aureus* and Table 3 for *C. albicans*.

Table 1

I. 1,1,1-trifluoroheptandione-2,4
II. 1,1,1-trifluorooctandione-2,4
III. 1,1,1-trifluorodecandione-2,4
IV. 1,1,1-trifluoropentadecandione-2,4
V. 1,1,1-trifluoroheptadecandione-2,4
VI. 1,1,1-trifluoroheneicosandione-2,4
VII. undecylenoic acid sodium salt (control)

TABLE 2

| Compound | (*S. aureus*, bacteria) Concentration | | | | | | | | |
|---|---|---|---|---|---|---|---|---|---|
| | 500 | 150 | 125 | 63 | 31 | 16 | 8 | 4 | 2 |
| I | − | + | + | + | + | + | + | + | + |

TABLE 2-continued (S. aureus, bacteria)

| Compound | Concentration | | | | | | | | |
|---|---|---|---|---|---|---|---|---|---|
| | 500 | 150 | 125 | 63 | 31 | 16 | 8 | 4 | 2 |
| II. | − | + | + | + | + | + | + | + | + |
| III. | − | − | − | ± | + | + | + | + | + |
| IV. | − | − | − | − | − | − | ± | + | + |
| V. | − | − | − | − | − | − | ± | + | + |
| VI. | − | − | − | − | − | + | + | + | + |
| VII. | − | + | + | + | + | + | + | + | + |

TABLE 3

(C. albicans, fungus)

| Compound | Concentration | | | | | | | | |
|---|---|---|---|---|---|---|---|---|---|
| | 500 | 250 | 125 | 63 | 31 | 16 | 8 | 4 | 2 |
| I. | − | − | − | − | − | − | − | − | − |
| II. | − | − | − | − | − | − | − | − | − |
| III. | − | − | ± | + | + | + | + | + | + |
| IV. | − | − | − | − | − | − | − | − | − |
| V. | − | − | − | − | − | − | − | − | − |
| VI. | + | + | + | + | + | + | + | + | + |
| VII. | + | + | + | + | + | + | + | + | + |

EXAMPLE 3

A tube containing 10 ml Trypticase Soy Broth and 10 parts per million 1,1,1-trifluoropentadecanedione-2,4 is inoculated with $5.3 \times 10^5$ S. aureus organisms. (The number of organisms is determined by serial dilution and plate count). A control tube, without the above beta-diketone, is inoculated with $4.7 \times 10^5$ organisms. The culture tubes are incubated at 37.5° C. and 1 ml samples are withdrawn from each tube at hourly intervals for six hours. These samples are serially diluted and plated to determine the number of viable colony forming units given in Table 4 as counts.

TABLE 4

| Hour | Control | Culture plus beta-diketone |
|---|---|---|
| 1 | $4.5 \times 10^5$ | $3.5 \times 10^5$ |
| 2 | $9.8 \times 10^5$ | $5.4 \times 10^5$ |
| 3 | $1.5 \times 10^6$ | $5.2 \times 10^5$ |
| 4 | $3.7 \times 10^6$ | $4.1 \times 10^5$ |
| 5 | $3.3 \times 10^7$ | $5.0 \times 10^5$ |
| 6 | $1.1 \times 10^8$ | $4.3 \times 10^5$ |

It will be noted that the count for the tube containing the beta-diketone is substantially constant within reasonable limits of error whereas the culture in the control table has increased about one thousand-fold. At the end of 24 hours, the control tube is turbid to the degree of being opaque, while the tube containing the beta-diketone is clear and has only a slight amount of material visible upon shaking (probably due to the original inoculum).

What is claimed is:

1. The process of inhibiting the growth of bacteria on the animal body, other than the oral cavity, and on inanimate surfaces which comprises providing in the environment of said bacteria a growth inhibiting amount of a beta-diketone compound represented by the formula $$Y-CO-CH_2-CO-R_f$$

wherein Y is an alkyl group having 5 to 20 carbon atoms, an alkenyl group having 5 to 20 carbon atoms, a halogen-substituted alkyl group having 5 to 20 carbon atoms, a halogen-substituted alkenyl group having 5 to 20 carbon atoms, a phenyl or naphthyl group or their halogen-substituted derivatives, and $R_f$ is a perfluoroalkyl group containing one to three carbon atoms.

2. The process for inhibiting the growth of bacteria according to claim 1 wherein $R_f$ is $CF_3$.

3. The process according to claim 2 wherein said beta-diketone is 1,1,1-trifluoropentadecandione-2,4.

4. The process according to claim 2 wherein said beta-diketone is 1,1,1-trifluoroheptadecandione-2,4.

5. A process for inhibiting the growth of bacteria according to claim 1 wherein said bacteria to be controlled are staphylococcus or streptococcus organisms.

6. A process according to claim 1 wherein said beta-diketone compound is in admixture with a vehicle.

7. The process of inhibiting the growth of fungi organisms on the animal body and on inanimate surfaces which comprises providing in the environment of said organisms a growth inhibiting amount of a beta-diketone compound represented by the formula $$Y-CO-CH_2-CO-R_f$$

wherein Y is selected from the group consisting of an alkyl group having 3 to 15 carbon atoms, an alkenyl group having 3 to 15 carbon atoms, a halogen-substituted alkyl group having 3 to 15 carbon atoms, and a halogen-substituted alkenyl group having 3 to 15 carbon atoms, and $R_f$ is a perfluoroalkyl group containing one to three carbon atoms.

8. A process for inhibiting the growth of fungi according to claim 7 wherein $R_f$ is $CF_3$.

9. The process according to claim 7 wherein said beta-diketone is 1,1,1-trifluoroheptandione-2,4.

10. The process according to claim 7 wherein said beta-diketone is 1,1,1-trifluorooctandione-2,4.

11. The process according to claim 7 wherein said beta-diketone is 1,1,1-trifluoropentadecandione-2,4.

12. The process according to claim 7 wherein said beta-diketone is 1,1,1-trifluoroheptadecandione-2,4.

13. A process for inhibiting the growth of a fungus according to claim 7 wherein said fungus to be controlled is of the species *Candida albicans*.

14. A process according to claim 7 wherein said beta-diketone compound is in admixture with a vehicle.

* * * * *

UNITED STATES PATENT AND TRADEMARK OFFICE
CERTIFICATE OF CORRECTION

PATENT NO. : 4,322,441
DATED : March 30, 1982
INVENTOR(S) : Michael R. Engel and Jill P. Stiller It is certified that error appears in the above—identified patent and that said Letters Patent is hereby corrected as shown below:

Column 2, line 28, replace "257,700" with -- 259,700 --.

Signed and Sealed this

Twentieth Day of July 1982

[SEAL]

Attest:

GERALD J. MOSSINGHOFF

Attesting Officer

Commissioner of Patents and Trademarks